United States Patent
Kihara

(10) Patent No.: US 10,455,239 B2
(45) Date of Patent: Oct. 22, 2019

(54) INFORMATION DISPLAY PROCESSING DEVICE AND CONTROL PROGRAM FOR INFORMATION DISPLAY PROCESSING DEVICE

(71) Applicant: Shimadzu Corporation, Kyoto-shi, Kyoto (JP)

(72) Inventor: Takayuki Kihara, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 128 days.

(21) Appl. No.: 15/123,166

(22) PCT Filed: Mar. 5, 2014

(86) PCT No.: PCT/JP2014/055598
§ 371 (c)(1),
(2) Date: Sep. 1, 2016

(87) PCT Pub. No.: WO2015/132900
PCT Pub. Date: Sep. 11, 2015

(65) Prior Publication Data
US 2017/0078679 A1 Mar. 16, 2017

(51) Int. Cl.
*G06K 9/00* (2006.01)
*H04N 19/186* (2014.01)
(Continued)

(52) U.S. Cl.
CPC ....... *H04N 19/186* (2014.11); *G06F 11/0739* (2013.01); *G06F 11/0766* (2013.01); *H04N 19/182* (2014.11); *G01N 30/8651* (2013.01)

(58) Field of Classification Search
None
See application file for complete search history.

(56) References Cited

U.S. PATENT DOCUMENTS 5,829,895 A * 11/1998 Hayashi ............... G06K 1/121
400/124.05
6,614,915 B2 * 9/2003 Powell ............... G06Q 20/341
382/100
(Continued)

FOREIGN PATENT DOCUMENTS

CN 102034127 A 4/2011

OTHER PUBLICATIONS

Written Opinion of the International Searching Authority dated May 20, 2014, issued in counterpart International Application No. PCT/JP2014/055598 (7 pages).
(Continued)

*Primary Examiner* — Randolph I Chu
(74) *Attorney, Agent, or Firm* — Westerman, Hattori, Daniels & Adrian, LLP

(57) ABSTRACT

In an information display processing device 1 for displaying a predetermined process result on a screen 14 of a display unit, the present device includes an encoding section 34 for creating a code image by encoding a piece of information held in the device and a display control section 35 for displaying, on the screen, the code image created by the encoding section 34 and a single identification header in a predetermined positional relationship to the code image, whereby the device reduces the processing load on a computer caused by an image search in a system which assists user operations through an image recognition process on a software basis.

22 Claims, 8 Drawing Sheets

(51) Int. Cl.
*G06F 11/07* (2006.01)
*H04N 19/182* (2014.01)
*G01N 30/86* (2006.01)

(56) References Cited

U.S. PATENT DOCUMENTS

| | | | | |
|---|---|---|---|---|
| 6,687,384 | B1* | 2/2004 | Isnardi | H04N 21/23892 |
| | | | | 375/E7.018 |
| 6,769,041 | B2* | 7/2004 | Dahlen | G06F 1/26 |
| | | | | 365/149 |
| 7,236,610 | B1* | 6/2007 | Luo | G06F 21/16 |
| | | | | 348/E5.006 |
| 9,165,538 | B2* | 10/2015 | Stoye | G09G 5/395 |
| 2004/0060990 | A1* | 4/2004 | Hilton | G06K 9/18 |
| | | | | 235/494 |
| 2004/0247874 | A1* | 12/2004 | Ryzi | G03H 1/0244 |
| | | | | 428/410 |
| 2005/0114685 | A1* | 5/2005 | Blinick | G06F 8/65 |
| | | | | 713/191 |
| 2008/0069396 | A1* | 3/2008 | He | G06T 1/0028 |
| | | | | 382/100 |
| 2009/0050700 | A1* | 2/2009 | Kamijoh | G06K 17/0022 |
| | | | | 235/440 |
| 2011/0083108 | A1* | 4/2011 | Klein | G06F 3/0481 |
| | | | | 715/859 |
| 2011/0194727 | A1* | 8/2011 | Guo | G06T 1/0021 |
| | | | | 382/100 |
| 2011/0242116 | A1* | 10/2011 | Nath | G09G 5/363 |
| | | | | 345/522 |
| 2011/0311042 | A1* | 12/2011 | Cheddad | G06F 21/602 |
| | | | | 380/28 |
| 2012/0167146 | A1* | 6/2012 | Incorvia | H04N 21/234318 |
| | | | | 725/60 |
| 2012/0304089 | A1* | 11/2012 | Cohen | G06F 11/0766 |
| | | | | 715/764 |
| 2013/0202199 | A1* | 8/2013 | Geisler | G06T 3/4007 |
| | | | | 382/159 |
| 2013/0322704 | A1* | 12/2013 | Harrison | G06K 9/00885 |
| | | | | 382/115 |
| 2014/0016817 | A1* | 1/2014 | Nakagata | H04N 19/467 |
| | | | | 382/100 |
| 2014/0047475 | A1* | 2/2014 | Oh | H04N 21/4355 |
| | | | | 725/40 |
| 2016/0320920 | A1* | 11/2016 | Morris | G06F 3/0488 |
| 2016/0335744 | A1* | 11/2016 | Saber | G09G 5/10 |
| 2017/0018219 | A1* | 1/2017 | Wang | G09G 3/2092 |
| 2017/0168997 | A1* | 6/2017 | Mess | G06F 17/30893 |

OTHER PUBLICATIONS

Ono, "RocketMouse Pro v8.5", [online], <URL:http://mojosoft.biz/products/rocketmousepro/>, Apr. 27, 2012, Mojosoft Co. Ltd., [accessed on Jan. 24, 2014], pp. 1-2 (cited in the specification).
Yamamoto, "AutoMouse", [online], <URL:http://www.vector.co.jp/soft/win95/util/se074062.html>, Mar. 2, 2001, [accessed on Jan. 24, 2014], pp. 1-2, (cited in the specification).
International Search Report dated May 20, 2014, issued in counterpart International Application No. PCT/JP2014/055598 (1 page).
Office Action dated Aug. 14, 2018, issued in counterpart Chinese Application No. 201480076834.9, with English translation (24 pages).

\* cited by examiner

Fig. 2A
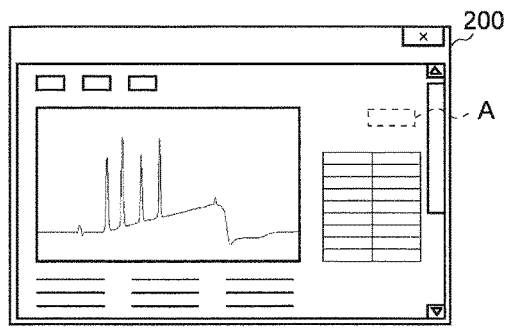
Fig. 2B
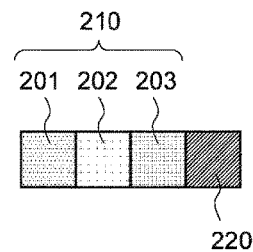
Fig. 3A
| | | R | G | B |
|---|---|---|---|---|
| IDENTIFICATION HEADER | 1ST PIXEL | 201 | 201 | 201 |
| | 2ND PIXEL | 199 | 199 | 199 |
| | 3RD PIXEL | 202 | 202 | 202 |
Fig. 3B
| LIQUID SUPPLY MODE | 4TH PIXEL | | |
|---|---|---|---|
| | R | G | B |
| ISOCRATIC | 201 | 200 | 200 |
| BINARY | 202 | 200 | 200 |
| LOW-PRESSURE GRADIENT ELUTION | 203 | 200 | 200 |
Fig. 4
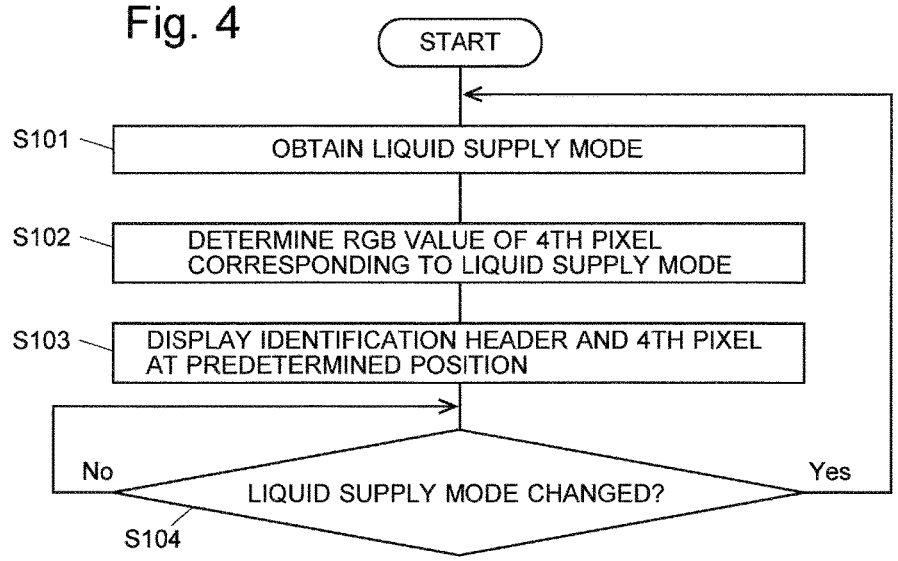

Fig. 9
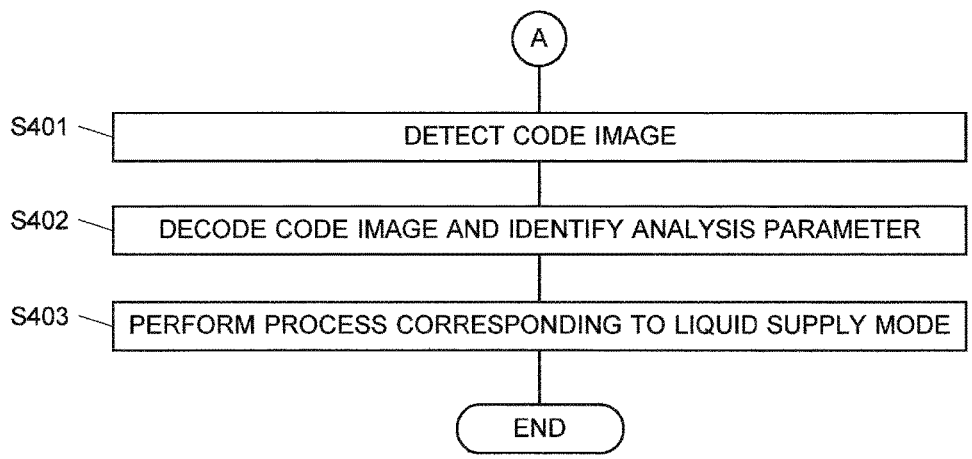
Fig. 10
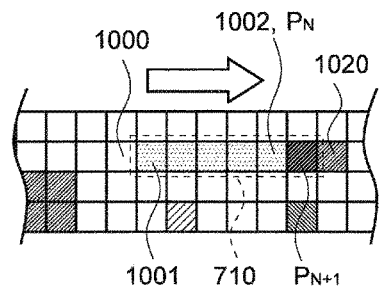
Fig. 11
| N VALUE | P = 20 | P = 50 | P = 90 |
|---|---|---|---|
| N | 0.8 + 0.4 / N | 0.5 + 1 / N | 0.1 + 1.8 / N |
| 3 | 0.93 | 0.83 | 0.70 |
| 6 | 0.87 | 0.67 | 0.40 |
| 10 | 0.84 | 0.60 | 0.28 |
| 20 | 0.82 | 0.55 | 0.19 |
Fig. 12
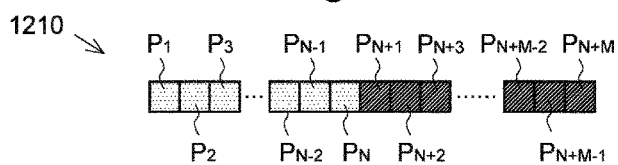

Fig. 14
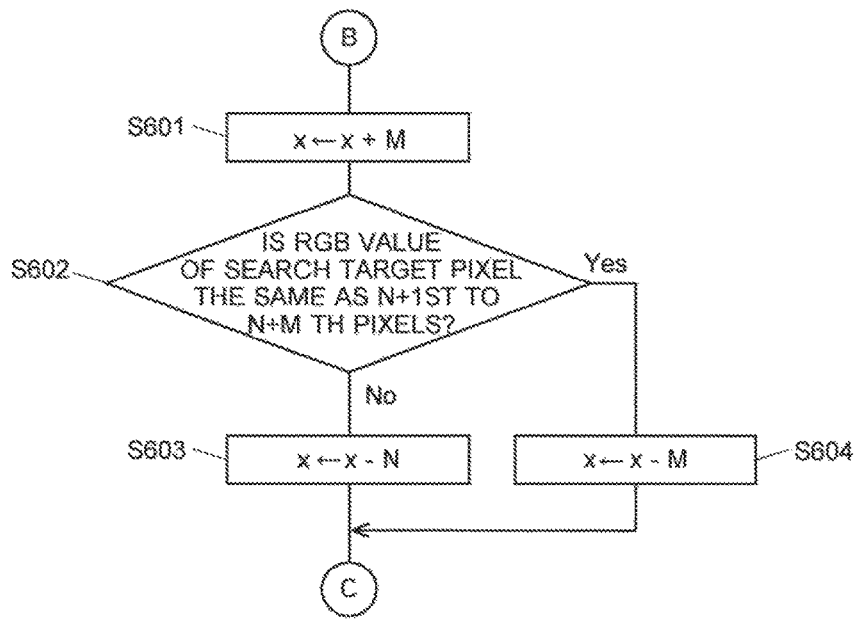
Fig. 15
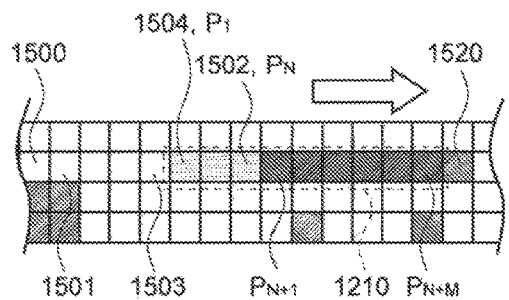
Fig. 16
| N VALUE | M VALUE | P = 20 | P = 50 | P = 90 |
|---|---|---|---|---|
| N | M | $1.6/(M-N) + 0.4/N$ | $1/(M-N) + 1/N$ | $0.2/(M-N) + 1.8/N$ |
| 3 | 6 | 0.67 | 0.67 | 0.67 |
| 6 | 12 | 0.33 | 0.33 | 0.33 |
| 10 | 20 | 0.20 | 0.20 | 0.20 |
| 20 | 40 | 0.10 | 0.10 | 0.10 |

INFORMATION DISPLAY PROCESSING DEVICE AND CONTROL PROGRAM FOR INFORMATION DISPLAY PROCESSING DEVICE

TECHNICAL FIELD

The present invention relates to an information display processing device, an operation-assisting device and similar device for assisting user operations through an image recognition process on a software basis.

BACKGROUND ART

In recent years, the tasks of controlling an analyzing apparatus as well as analyzing data obtained as a result of an analysis have been conducted using a controlling and analyzing software program which runs on a commonly used computer. Main users of such software products are analysis operators who actually use analyzing devices.

Users are not always proficient in the operation of such software. Therefore, even a software program which seems to be equipped with a satisfactory set of functions from the viewpoint of the developer may afterwards turn out to be in need of additional functions (e.g. buttons, descriptions or other GUI elements). Furthermore, although the contents of the errors that may possibly occur can to some extent be grasped in the development phase, it may be impossible for the developer to prepare a sufficient amount of support information on the measures to be taken when an error has occurred. Indeed, users cause errors under various situations. If an error has occurred in an unexpected situation for the developer, it may be difficult for users to find an appropriate recovery method from the descriptions prepared before the selling of the product. In this way, it is often the case that the addition of a function or support information is desired after the software is offered to users as the product.

In light of such a situation, the present inventor has conceived the idea of installing an operation-assisting program apart from a main software program on a computer, where the operation-assisting program is configured to detect a specific image displayed by the main software and then display additional GUI elements or similar pieces of information.

There are also other conventional techniques for offering some forms of assistance to user operations by detecting an image displayed on a screen. For example, Non Patent Literature 1 discloses a technique including the steps of searching the screen for an image which matches with an image previously registered by a user and automatically performing a click operation in the located image. Non Patent Literature 2 also discloses a similar technique, which is further capable of detecting similar images based on the pattern recognition.

CITATION LIST

Non Patent Literature

Non Patent Literature 1: Kakuya Yamamoto, "AutoMouse", [online], Mar. 2, 2001, [accessed on Jan. 24, 2014], the Internet Non Patent Literature 2: Takahiro Ono, "RocketMouse Pro v8.5", [online], Apr. 27, 2012, Mojosoft Co. Ltd., [accessed on Jan. 24, 2014], the Internet,

SUMMARY OF INVENTION

Technical Problem

Such an image search based on the matching determination is likely to cause the problem of a high processing load on the computer. For example, even the process of searching for a perfect-matching image as in Non Patent Literature 1 may require a considerable amount of computation depending on the size of the image to be located. Similarly, when a plurality of images need to be simultaneously searched for, the number of pixels to be compared in the matching determination increases, so that the CPU (central processing unit) utilization can easily reach the upper limit and cause such problems as the stagnation of the processing of the main program. In general, a system for conveying various kinds of information through image recognition requires the suppression of the processing load caused by the image search since there may be the situation in which a number of images are simultaneously searched for to deal with many pieces of information and various conditions.

The present invention has been developed in view of the previously described situations. Its objective is to provide an information display processing device, operation-assisting device and similar device for reducing the processing load on a computer caused by the image search in a system which assists user operations through an image recognition process on a software basis.

Solution to Problem

The first aspect of the present invention developed for solving the previously described problem is an information display processing device for displaying a predetermined process result on a screen of a display unit, including:

a) an encoding section for creating a code image by encoding a piece of information held in the device; and b) a display control section for displaying, on the screen, the code image created by the encoding section and a single identification header in a predetermined positional relationship to the code image.

According to the previously described configuration, a specified item of information held by the information display processing device is encoded into a code image by the encoding section. The code image is displayed on the screen of the display unit, along with a single identification header, by the display control section. Since the identification header is in a predetermined positional relationship to the code image, an operation-assisting program used for assisting the user of the information display processing device only needs to search for the identification header so as to detect the code image based on the previously set positional relationship and decode the code image to obtain the specified item of information. In other words, it is unnecessary to directly search for the code image.

The identification header only needs to hold information which enables locating the code image. Therefore, in most cases, it has a smaller amount of information than the amount of information represented by the code image. Accordingly, the operation-assisting program can detect the code image with a smaller amount of computation as compared to the case of directly searching for the code image. Consequently, the processing load on the computer caused by the image search is reduced.

Examples of the information encoded by the encoding section include: the content of an error which has occurred in the information display processing device; and analysis parameters used by the information display processing device if this device is configured to control an analyzing apparatus.

In a preferable mode of the present invention, the code image and the identification header are composed of a plurality of pixels having color differences which are difficult to be visually recognized by users; and the display control section displays the code image and the identification header in a uniformly-colored area within a designated region occupied by a color close to the plurality of pixels.

According to this configuration, the code image and the identification header become difficult to be visually recognized on the screen, and therefore, will neither deteriorate the visibility of other objects nor make users feel uncomfortable.

The identification header may include a first pixel group composed of N uniformly-colored pixels sequentially arranged in a row direction and a second pixel group neighboring the first pixel group in the same row, with the second pixel group composed of one or a plurality of pixels having a different color from the first pixel group, where N is a natural number equal to or greater than three.

According to this configuration, the identification header includes the first pixel group and the second pixel group neighboring each other in the row direction. Each group is composed of uniformly-colored pixels, while the two groups differ from each other in pixel color. The first pixel group is composed of N pixels sequentially arranged in the row direction.

Accordingly, for example, the operation-assisting program can be configured as follows: in the process of searching the screen of the display unit in the direction from the first pixel group to the second pixel group, when two successive pixels having different colors are detected, the program assumes that the succeeding pixel in the searching direction among the two pixels is the first pixel of the second pixel group, and verifies this assumption. If the verification has revealed that the assumption is false, the searching point is moved forward by N columns. Every time the assumption is found to be false, the operation-assisting program can bypass N−1 pixels in the search. The total number of pixels bypassed in the search increases with the degree of non-uniformity in the color of the pixels on the screen of the display unit. Consequently, the processing load caused by the image search is further reduced.

The second pixel group may be composed of M uniformly-colored pixels sequentially arranged in the row direction, where M is a natural number greater than N.

According to this configuration, the first pixel group in the identification header is composed of N pixels sequentially arranged in the row direction, and the second pixel group is composed of M pixels sequentially arranged in the row direction, where N<M. In this case, for example, the previously described operation-assisting program can additionally perform the following process: When two successive pixels having the same color are detected, the program assumes that these two pixels are the first two pixels of the second pixel group or two other pixels located close to them in the row, and moves the searching point forward from the succeeding one of the two pixels by M columns. If the color of the pixel which is reached after this movement is the same as that of the second pixel group, the searching point is returned to the original pixel, whereas the searching point is moved to the position which is M−N+1 columns ahead of the original pixel if the two colors are not the same. Every time the assumption is found to be false, the operation-assisting program can bypass M−N pixels in the search. If the value of M is appropriately set, the processing load caused by the image search will be even further reduced.

The second aspect of the present invention developed for solving the previously described problem is an operation-assisting device for assisting user operations related to a piece of target software, including:

a) an identification-header detection section for detecting a single identification header displayed on a screen of a display unit;

b) a code-image detection section for detecting, based on a positional relationship with the identification header detected by the identification-header detection section, a code image in which a specified item of information related to the target software is held in a coded form;

c) a decoding section for decoding the code image detected by the code-image detection section, to obtain the specified item of information; and d) an execution section for performing a specified process associated with the specified item of information obtained by the decoding section.

According to the previously described configuration, after the identification-header detection section has detected the single identification header, the code-image detection section detects a code image in which a specified item of information is held in a coded form, based on the positional relationship with the identification header. The detected code image is decoded by the decoding section. The execution section performs a specified process associated with the specified item of information obtained by the decoding. In other words, the operation-assisting device only needs to search for the single identification header and does not need to directly search for the code image.

The identification header only needs to hold information which enables locating the code image. Therefore, in most cases, it has a smaller amount of information than the amount of information represented by the code image. Accordingly, the operation-assisting device can detect the code image with a smaller amount of computation as compared to the case of directly searching for the code image. Consequently, the processing load on the computer caused by the image search is reduced.

The identification-header detection section may be configured as follows: for a natural number N equal to or greater than three, the identification-header detection section searches the screen in the row direction, examining the value of each pixel, and if a pixel whose color differs from the preceding pixel is detected, the identification-header detection section determines whether or not the detected pixel is the pixel in the N+1st column of the identification header, and if the determination result is negative, the identification-header detection section resumes the search from a pixel which is N columns far ahead of the detected pixel.

According to this configuration, the operation-assisting program can bypass N−1 pixels in the search every time a pixel whose color differs from the preceding pixel is detected and if this detected pixel is found to be not the pixel in the N+1st column of the identification header. The total number of pixels bypassed in the search increases with the degree of non-uniformity in the color of the pixels on the screen of the display unit. Accordingly, the processing load caused by the image search will be even further reduced if the target software includes, as the identification header, an image which includes a first pixel group composed of N uniformly-colored pixels sequentially arranged in a row direction and a second pixel group neighboring the first pixel group in the same row, with the second pixel group composed of one or a plurality of pixels having a different color from the first pixel group.

The identification-header detection section may additionally be configured as follows: for a natural number M greater than N, if a pixel having the same color as the preceding pixel is detected, the identification-header detection section determines whether or not the color of the pixel located M columns far ahead of the detected pixel is the same as the color of the pixels in the N+1st through N+Mth columns of the identification header, and then resumes the search from the pixel located immediately after the detected pixel if it is determined that the two colors are the same, or from the pixel located M−N+1 columns far ahead of the detected pixel if it is determined that the two colors are different from each other.

According to this configuration, the operation-assisting program can bypass M−N pixels in the search every time a pixel whose color is the same as the preceding pixel is detected and if the pixel located M columns far ahead of the detected pixel is found to have a color that is different from the pixels in the N+1st through N+Mth columns of the identification header. The total number of pixels bypassed in the search increases with the degree of non-uniformity in the color of the pixels on the screen of the display unit. Accordingly, the processing load caused by the image search will be even further reduced if the target software uses, as the identification header, an image which includes a first pixel group composed of N uniformly-colored pixels sequentially arranged in a row direction and a second pixel group neighboring the first pixel group in the same row, with the second pixel group composed of M pixels having a uniform color different from the first pixel group, and if the value of M is appropriately set.

Advantageous Effects of the Invention

According to the first and second aspects of the present invention, the processing load on a computer caused by the image search is reduced in a system which assists user operations through an image recognition process on a software basis.

BRIEF DESCRIPTION OF DRAWINGS

FIG. 2A is an example of the screen display of a window of analysis control software displayed by the analysis control device according to the same embodiment, and FIG. 2B is one example of the identification header and code image displayed in area "A" in FIG. 2A.

FIG. 3A is one example of the RGB values of the identification header which the analysis control device according to the same embodiment embeds in a designated region occupied by pixels having an RGB value of (200, 200, 200) on the screen, and FIG. 3B is one example of the correspondence relationship between the RGB value of the code image which the analysis control device according to the same embodiment embeds in the aforementioned region and the liquid supply mode.

FIG. 4 is a flowchart showing one example of the flow of the code image embedding process performed by the analysis control device according to the same embodiment.

FIG. 9 is a flowchart showing the flow of a process performed when the identification header is detected in the flowchart shown in FIG. 8.

FIG. 10 is a diagram illustrating the image search performed by the analysis control device according to the same embodiment.

FIG. 11 is a comparison table showing the processing load required for the image search using the analysis control device according to the same embodiment.

FIG. 12 is one example of the identification header which an analysis control device according to the third embodiment of the present invention embeds in the screen.

FIG. 14 is a flowchart showing the flow of the process performed by the analysis control device according to the same embodiment when two successive pixels having the same color are detected.

FIG. 15 is a diagram illustrating the image search performed by the analysis control device according to the same embodiment.

FIG. 16 is a comparison table showing the processing load required for the image search using the analysis control device according to the same embodiment.

DESCRIPTION OF EMBODIMENTS

Modes for carrying out the present invention are hereinafter described in detail with reference to the drawings. In the following descriptions, components which have the same functions as those already shown in previously described drawings will be denoted by the same numerals, and their descriptions will be omitted.

First Embodiment

Figure 1:
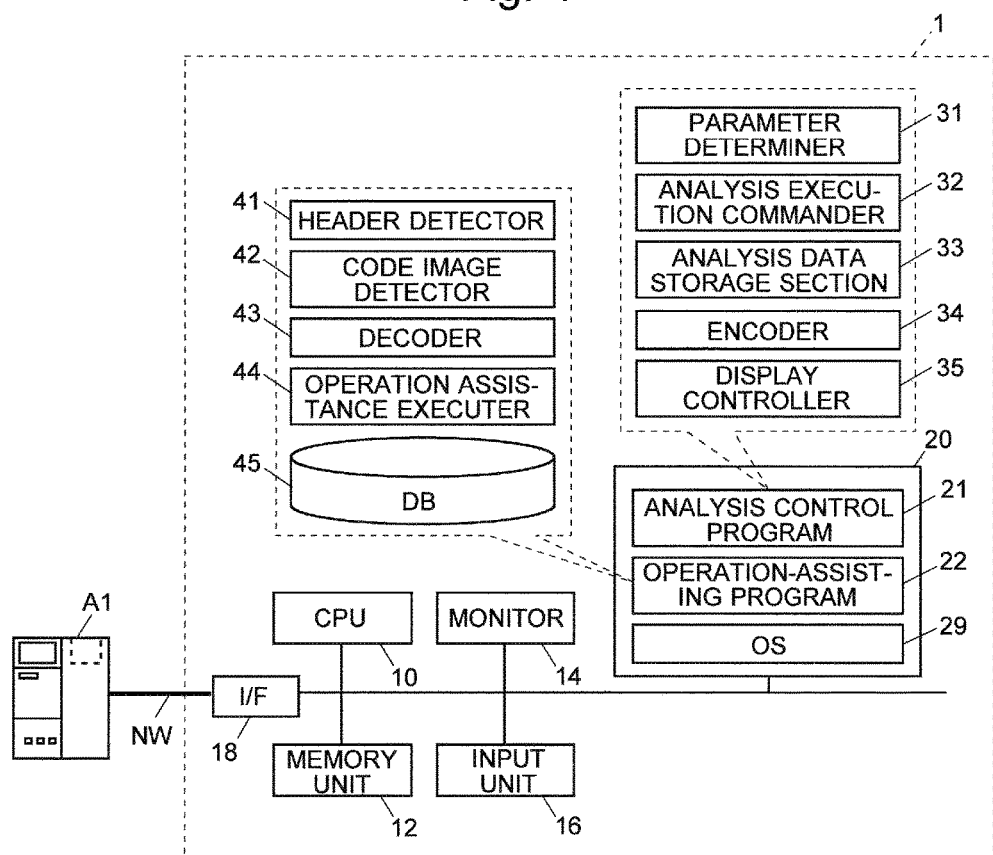
FIG. 1 is a block diagram showing the schematic configuration of an analysis control device according to the first embodiment of the present invention.

FIG. 1 shows an analysis control device (information display processing device, or operation-assisting device) 1 according to the first embodiment of the present invention. The analysis control device 1 is actually a computer including a CPU (central processing unit) 10 with the following units connected to each other: a memory unit 12; a monitor (display unit) 14, such as an LCD (liquid crystal display); an input unit 16 including a keyboard, mouse and/or other devices; and a storage unit 20. Among these units and devices, the memory unit 12 is a volatile storage device, such as a RAM (random access memory), while the storage unit 20 is constructed using a non-volatile storage device, such as a ROM (read only memory), flash memory, EPROM (erasable programmable ROM), EEPROM® (electrically EPROM), HDD (hard disk drive) or SSD (solid state drive). An analysis control program 21 and operation-assisting program 22 are provided in the storage unit 20. The components included in the analysis control program 21 and operation-assisting program 22 (which will be described later) are functional means realized by the CPU 10 loading those programs into the memory unit 12 and executing them. The OS (operating system) 29 is also stored in the storage unit 20.

The analysis control 1 is provided with an interface (I/F) 18 for controlling direct connections with external devices or network connections with external devices (or other devices) through the LAN (local area network) or the like. Through this interface 18, the analysis control device 1 is connected to an analyzer A1 via the network cable NW (or wireless LAN).

The analysis control device 1 may have a plurality of analyzers connected to it. The analysis control device 1 and the analyzer A1 may be configured as a single device.

In the present embodiment, the analyzer A1 is assumed to be a liquid chromatograph mass spectrometer (LC-MS). Actually, the analyzer A1 is not limited to this type of device; it may be a gas chromatograph (GC), liquid chromatograph (LC) or gas chromatograph mass spectrometer (GC-MS). The analyzer A1 may also be other kinds of experimental or medical devices. There is no limitation to the method or target of the measurement as long as the analyzer can be controlled or monitored by a computer.

The analysis control program 21 is a piece of application software for controlling the analysis performed by the analyzer A1. It determines various parameters, and commands the analyzer A1 to perform an analysis according to the parameters. The analysis control program 21 also displays, in real time, the result of the analysis performed by the analyzer A1 on the screen of the monitor 14.

In FIG. 1, a parameter determiner 31, analysis execution commander 32, analysis data storage section 33, encoder (encoding section) 34 and display controller (display control section) 35 are shown in relation to the analysis control program 21. The analysis control program 21 may additionally has the function of acting as analysis software for analyzing the result of the analysis performed by the analyzer A1. However, this topic is unrelated to the spirit of the present invention and therefore will not be shown or described.

The parameter determiner 31 determines various parameters for the analysis performed by the analyzer A1 based on the information given by users through the input unit 16. For example, the parameters include temperature, pressure, liquid supply mode of the pump, flow rate of the pump, etc. The parameters may be changeable in the middle of the analysis by the analyzer A1.

The analysis execution commander 32 notifies the analyzer A1 of the analysis parameters determined by the parameter determiner 31, and commands the analyzer A1 to perform an analysis according to the given analysis parameters. The notification and command are given through the I/F 18.

The analysis data storage section 33 is a storage area in which the result of the analysis performed by the analyzer A1 based on the command is stored as analysis data.

The encoder 34 creates a code image by encoding a specified item of information held in the analysis control program 21. Examples of the specified item of information include the parameters determined by the parameter determiner 31, the analysis result stored in the analysis data storage section 33, and the content of an error which has occurred in the analysis control program 21. As the code image, one or more pixels with different RGB values assigned according to the content of the information may be used, or a binary image which can be encoded and decoded by commonly known algorithms may be used, such as the QR Code®. The former type is available in the case where the information to be encoded can take only a small number of different values, while the latter type is suitable in the case where the information concerned is a continuous variable, character string or similar form of information that cannot be easily represented using a limited range of RGB values. It is also possible to divide an image of the QR Code having a plurality of rows into image strips, with each strip corresponding to one row, and concatenate those strips into a single row to be used as the code image.

The display controller 35 sends the monitor 14 video signals containing various kinds of information processed by the analysis control program 21. Specifically, it creates an image which shows analysis data processed into a specific form (e.g. a graph) by an analysis data processing section (not shown) in the analysis control program 21, and displays that image on the screen of the monitor 14, as shown in FIG. 2A. FIG. 2A is one example of the window 200 of the analysis control program 21 displayed on the screen of the monitor 14 by the display controller 35. Additionally, as a feature of the present embodiment, the display controller 35 displays the code image created by the encoder 34 at a predetermined position on the screen (e.g. within the area "A" surrounded by the broken line in FIG. 2A), with an identification header (which will be described later) added to the code image. In the following description, the operation of displaying the identification header and the code image on the screen is called the "embedding". A typical location at which the identification header and the code image are embedded is a blank area occupied by a predetermined background color. The location should preferably be chosen so that neither the identification header nor the code image will overlap specific objects.

The identification header in the present embodiment is hereinafter described.

An identification header is a piece of information for helping an operation-assisting program 22 (which will be described later) detect the code image displayed on the screen of the monitor 14. In other words, the identification header is a special array pattern which can be easily detected, and one which is located at a predefined relative position to the code image. FIG. 2B shows one specific example: for a single pixel 220 serving as the code image, an identification header 210 consisting of three successive pixels 201-203 having different predetermined RGB values is assigned, with one end of the header adjacent to the pixel 220 in the row direction. FIG. 2B is an enlarged view of an image within the area "A" in FIG. 2A, in which the identification header 210 and the fourth pixel (code image) 220 embedded in the area "A" are shown.

As a feature of the present embodiment, the identification header and the code image are displayed in such colors that are difficult to be visually distinguished by users when embedded in the screen; i.e. they have RGB values whose color differences from the neighboring pixels at the display position are extremely small so that users cannot visually recognize the difference.

A specific example is described with reference to FIGS. 3A and 3B. It is assumed that the identification header 210 and the fourth pixel 220 are embedded in area "A" in FIG. 2A, and this area "A" is entirely occupied by pixels having an RGB value of (200, 200, 200), which is the background color of the window 200. The monitor 14 is capable of the 256-gradation expression for each of the R, G and B colors.

FIG. 3A is a table showing the RGB values of the pixels of the identification header 210 to be embedded in the screen of the monitor 14 by the display controller 35. As shown, the RGB values of (201, 201, 201), (199, 199, 199) and (202, 202, 202) are respectively assigned to the first pixel 201, second pixel 202 and third pixel 203. These values are fixed and independent of the liquid supply mode.

On the other hand, the fourth pixel 220 is given an RGB value which changes depending on the liquid supply mode. FIG. 3B is a table showing the correspondence relationship between the RGB value of the fourth pixel 220 and the liquid supply mode. There are three liquid supply modes: isocratic mode, binary mode and low-pressure gradient elution mode. Depending on these modes, an RGB value of (201, 200, 200), (202, 200, 200) or (203, 200, 200) is respectively assigned to the fourth pixel 220. In the shown example, only the R value is changed according to the liquid supply mode. Needless to say, it is possible to change the G or B value, or change two or all of them in combination.

As is evident from the RGB values in the previous example, the identification header 210 and the fourth pixel 220 have extremely small amounts of color difference from the pixels which are adjacent to them when they are embedded in the area "A". It is practically impossible for users to visually recognize the embedded image. By comparison, the operation-assisting program 22, which directly refers to the RGB values, can correctly recognize the color differences which are unrecognizable for users and detect the identification header 210. It can also correctly distinguish between the three possible states of the fourth pixel 220. Thus, the display controller 35 can embed a piece of coded information in the screen without deteriorating the visibility of other objects on the screen or making users feel uncomfortable. The QR Code can also be similarly used as the code image by replacing the colors of the pixels forming the QR Code (which is normally expressed by a two-level gradation) with appropriate RGB values which make the code image difficult to be visually recognized by users.

The previously mentioned RGB values are mere examples. Their actual values should be appropriately set for each specific area in which those pixels will be displayed. In most cases, a set of values representing a color that is close to the blank area which occupies the largest area in the window 200 of the analysis control program 21 will be a practically appropriate choice, because it provides a high degree of freedom of the display location. From the viewpoint of the prevention of an incorrect detection, the pixels in the identification header 210 should preferably have RGB values that form a color array which is rarely used on the screen. From the same viewpoint, the identification header should be composed of three or more pixels.

As in the case of the QR Code, when the code image is composed of a large number of pixels, a pixel which shows size information of the code image according to a predefined rule may be appended to the identification header so that the operation-assisting program 22 can correctly detect the code image. For example, if there are a plurality of possible sizes for the code image, a different RGB value can be assigned to each size. The pixel representing the size information may be a pixel included in the code image or a pixel independent of the code image.

Once more referring to FIG. 1, the operation-assisting program 22 provided in the storage section 20 of the analysis control device 1 is described.

The operation-assisting program 22 is a program for assisting user operations on the analysis control program 21. The operation-assisting program 22 may be additionally installed on a computer on which the analysis control program 21 has already been installed, or it may be simultaneously installed with the analysis control program 21.

In FIG. 1, a header detector (identification-header detection section) 41, code-image detector (code-image detection section) 42, decoder (decoding section) 43, operation assistance executer (execution section) 44 and database (DB) 45 are shown in relation to the operation-assisting program 22.

The header detector 41 detects the identification header displayed on the screen of the monitor 14. Specifically, for example, it scans the screen of the monitor 14 rightward from the upper left pixel, examining the RGB value of each pixel, to locate an image which matches the identification header. When the scan has reached the rightmost pixel, the scan point is moved to the leftmost pixel in the next row and the rightward scan is resumed.

The code-image detector 42 detects the code image. Specifically, based on the predetermined positional relationship between the identification header and the code image, it determines the position of the code image from the position of the identification header located by the header detector 41, and detects the code image displayed at the determined position.

The decoder 43 decodes the code image detected by the code-image detector 42 and obtains the original information. Specifically, if the information is encoded as the RGB value of the code image, the decoder 43 refers to a code correspondence table (stored in the database 45) in which RGB values of the code image are associated with specified items of information, and obtains the information associated with the RGB value of the code image detected by the code-image detector 42. For example, this code correspondence table has a data structure in the form of a table as shown in the already referenced FIG. 3B. If a QR Code or similar image which can be encoded and decoded by a commonly known algorithm is used, the decoder 43 can obtain the original information by using the corresponding decoding algorithm.

The operation assistance executer 44 performs a specified process based on the information obtained by the decoder 43. For example, if the information obtained is a currently applied analysis parameter, the specified process may be the display of a GUI element, such as a descriptive comment or specific button corresponding to that parameter. It will also be useful to urge the analysis control program 21 to display a setting window corresponding to the currently applied analysis parameter, if the message to be transmitted to the analysis control program 21 is previously known. As another example, if the information obtained by the decoder 43 includes the content of an error which has occurred, a comment for informing users of the procedure for recovering from the error may be displayed. These specified processes are determined with reference to an operation-assisting process correspondence table (stored in the database 45, although not shown) in which specified items of information are associated with specified processes.

The database 45 contains the code correspondence table which associates the code image with the specified item of information, and the operation-assisting process correspondence table which associates the specified item of information with the specified process. The code correspondence table is referenced by the decoder 43 to decode original information from the code image, while the operation-assisting process correspondence table is referenced by the operation assistance executer 44 to determine the operation to be performed based on that original information. The code correspondence table is dispensable in the case where the decoder 43 uses a commonly known decoding algorithm (e.g. a QR-Code reading technique) to decode the code image.

[Flow of Code Image Embedding Process]

Hereinafter, the flow of the code image embedding process by the analysis control program 21 of the present embodiment is described with reference to FIG. 4 which is a flowchart, as well as FIGS. 2A, 2B, 3A and 3B when needed. The present description deals with the previously described example of FIGS. 2A-3B. The code image embedding process by the analysis control program 21 may be initiated at the timing when the liquid supply mode has been determined by the parameter determiner 31 or at the timing when the analysis execution commander 32 has commanded the analyzer A1 to execute the analysis. Alternatively, the code image embedding process may be repeated at regular intervals of time.

Initially, the encoder 34 obtains the liquid supply mode (Step S101). Specifically, the encoder 34 obtains the parameter information determined by the parameter determiner 31 and extracts the parameter related to the liquid supply mode from the plurality of parameters.

Next, the encoder 34 determines the RGB value of the fourth pixel 220 according to the liquid supply mode (Step S102). Specifically, based on the correspondence relationship shown in FIG. 3B, the encoder 34 assigns, to the fourth pixel 220, the RGB value corresponding to the liquid supply mode. For the present, it is assumed that the liquid supply mode is the low-pressure gradient elution mode. The encoder 34 assigns (203, 200, 200) as the RGB value.

Next, the display controller 35 displays the identification header 210 and the fourth pixel 220 at a predetermined position (Step S103). Specifically, the display controller 35 embeds the four sequential pixels 201, 202, 203 and 220 shown in FIG. 2B at a predetermined position within the window 200 shown in FIG. 2A (e.g. within the area "A" occupied by pixels having an RGB value of (200, 200, 200), which is the background color of the window 200). The first three pixels constitute the identification header 210, with the RGB values of (201, 201, 201), (199, 199, 199) and (202, 202, 202) respectively assigned to the first pixel 201, second pixel 202 and third pixel 203, as shown in FIG. 3A. The fourth pixel 220 is given the RGB value determined in Step S102, i.e. (203, 200, 200). It should be noted that the position at which the identification header 210 and the fourth pixel 220 are displayed is not limited to area "A"; they may be displayed in any area which has the RGB value of (200, 200, 200) or close values over the entire or largest part of the area. In general, the blank areas in an application window are painted in a uniform color (background color). Therefore, in practice, the display controller 35 can embed the identification header 210 and the fourth pixel 220 in almost any blank area within the window 200.

At a later point in time, if the liquid supply mode is changed by the parameter determiner 31 ("Yes" in Step S104), the code image embedding process returns to Step S101, and the encoder 34 obtains the updated information on the liquid supply mode. While there is no change in the liquid supply mode ("No" in Step S104), the display controller 35 maintains the display with the identification header 210 and the fourth pixel 220 embedded. As an alternative example, the display controller 35 may discontinue this display after the passage of a predetermined length of time from Step S103.

According to the processes described to this point, the analysis control program 21 embeds the fourth pixel 220 in which the liquid supply mode is encoded as the RGB value in the screen of the monitor 14. The identification header 210 added to the fourth pixel 220 enables the operation-assisting program 22 to indirectly locate the fourth pixel 220 based on the predefined positional relationship by detecting the identification header 210. Since the identification header 210 and the fourth pixel 220 are given similar colors to the background color of the display area, they are difficult to be visually recognized by users, and therefore, will neither deteriorate the visibility of other objects nor make users feel uncomfortable.

[Flow of Searching and Operation-Assisting Process]

Figure 5:
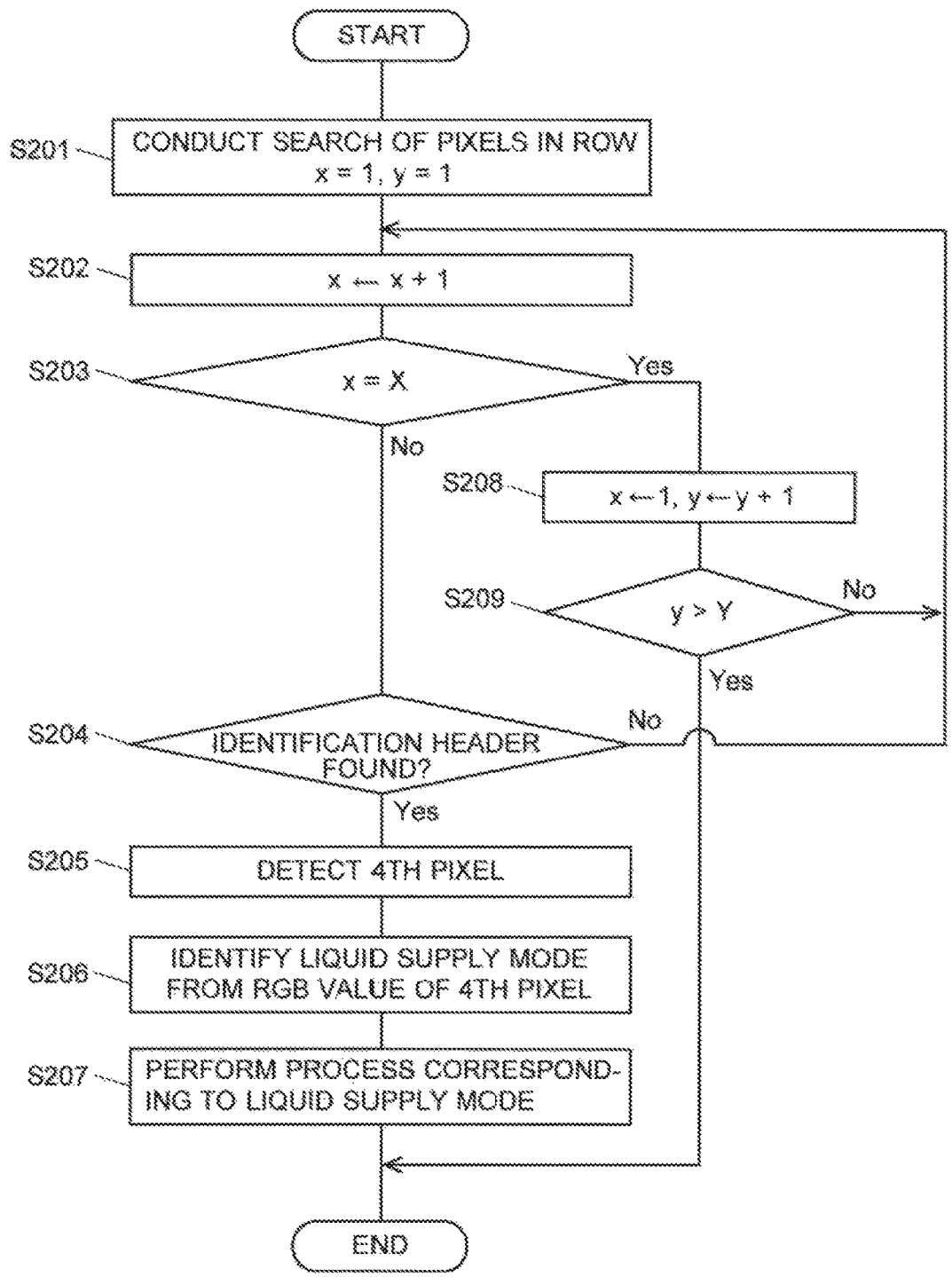
FIG. 5 is a flowchart showing one example of the flow of the searching and operation-assisting process performed by the analysis control device according to the same embodiment.
Figure 6:
FIG. 6 is an example of the screen display in which a GUI corresponding to the liquid supply mode is displayed as a result of the searching and operation-assisting process shown in FIG. 5.

Next, the flow of the searching and operation-assisting process by the operation-assisting program 22 in the present embodiment is described with reference to FIG. 5 which is a flowchart, as well as FIG. 6 when needed. The following description is premised on that the analysis control program 21 has already embedded the identification header 210 and the fourth pixel 220 in the window 200 by the previously described code image embedding process. The searching and operation-assisting process by the operation-assisting program 22 may be repeated at regular intervals of time or be performed in response to a user command. It is also possible to configure the system so that a command to initiate the searching and operation-assisting process is issued from the analysis control program 21 to the operation-assisting program 22 at a specific timing (e.g. when Step S103 is completed), with the operation-assisting program 22 configured to initiate the searching and operation-assisting process upon receiving this command.

Initially, the header detector 41 conducts the search of the pixels in a row from the upper left end of the screen (Step S201). Specifically, it refers to the RGB value of the leftmost pixel (1, 1) in the first row in a captured image of the screen of the monitor 14. The "captured image" is an image obtained by the screen-capturing function, which is provided in commonly used computer operating systems to create a copy of the displayed contents on the screen and store it in a temporary storage area. The header detector 41 requests the OS 29 to capture the screen of the monitor 14, and refers to the RGB values of the pixels in the captured image. The captured image is X pixels wide and Y pixels high.

The header detector 41 searches the row rightward, referring to the RGB values of the pixels (Step S202), to determine whether or not an image which matches the identification header 210, i.e. three successive pixels which respectively have the RGB values of (201, 201, 201), (199, 199, 199) and (202, 202, 202), is present (Step S204). If the identification header 210 has not been located ("No" in Step S204), the process is returned to Step S202 to continue the search. When the search has reached the rightmost column of the captured image ("Yes" in Step S203), the matching determination is bypassed and the searching point is moved to the left end of the next row (Step S208) before returning to the Step S202 to continue the search. In Step S208, if the searching point has gone beyond the bottom row of the captured image ("Yes" in Step S209), it means that the entire image has been completely searched. Accordingly, the searching and operation-assisting process is discontinued.

The reason why the determination on the matching with the identification header 210 is bypassed when the search has reached the right end of the captured image ("Yes" in Step S203) is because, if the third pixel 203 of the identification header 210 is at the right end of the screen, the fourth pixel 220 is outside the screen and undetectable. In the case where the code image is W pixels wide by H pixels high, for example, the following formulae (1) and (2) are used for the determinations in Steps S203 and S209, respectively:

$$x > X - W \quad (1)$$

$$y > Y - H + 1 \quad (2)$$

The formulae (1) and (2) are intended for use with a code image whose upper left end is located at the pixel which immediately succeeds the identification header 210. It should be noted that those formulae need to be modified if the positional relationship between the identification header 210 and the code image is different.

When the identification header 210 is detected ("Yes" in Step S204), the code-image detector 42 subsequently detects the fourth pixel 220 (Step S205). Specifically, the search target pixel located immediately after (in the case of FIG. 2B, on the right side of) the third pixel 203 of the identification header 210 is recognized as the fourth pixel 220.

Next, the decoder 43 identifies the liquid supply mode from the RGB value of the fourth pixel 220 (Step S206). Specifically, it refers to the code correspondence table in the database 45 and identifies the liquid supply mode associated with the RGB value of the fourth pixel 220 detected by the code-image detector 42. More specifically, the decoder 43 searches the code correspondence table for a record in which the data value held in the field showing the RGB value of the fourth pixel matches with the RGB value of the pixel detected by the code-image detector 42 in Step S205, and refers to the data value in the field showing the liquid supply mode in the located record. Referring to FIG. 3B which is one example of the data structure of the code correspondence table, the record which has an RGB value of (203, 200, 200) as the data value in the "4th Pixel" field has a data value of "Low-Pressure Gradient Elution" in the "Liquid Supply Mode" field. Accordingly, the decoder 43 determines that the liquid supply mode is the low-pressure gradient elution mode.

Next, the operation assistance executer 44 performs a process corresponding to the liquid supply mode (Step S207). Specifically, it refers to the operation-assisting process correspondence table (stored in the database 45, although not shown) in which specified items of information are associated with specified processes, and performs the process associated with the liquid supply mode identified by the decoder 43. The liquid supply mode has already been identified as the low-pressure gradient elution mode in the Step S206. Accordingly, for example, a request for the display of a gradient-time-program setting window is sent to the analysis control program 21. FIG. 6 shows the state in which the gradient-time-program setting window 600 has been displayed as a result of the present step. As another example, an appropriate type of GUI element may be displayed on the screen, such as a description informing users of the currently applied liquid supply mode.

Thus, the searching and operation-assisting process is completed. In the case where the analysis control program 21 can embed a plurality of identification headers and code images, the system may be configured to return to Step S202 to further continue the search after Step S207.

According to the processes described to this point, the operation-assisting program 22 searches the screen of the monitor 14 for the identification header 210 and detects the fourth pixel 220 based on the predefined positional relationship after the identification header 210 is located. Based on the RGB value of the detected fourth pixel, the program identifies the liquid supply mode encoded by the encoder 34 and performs a specified process (e.g. the display of a GUI element) associated with the identified liquid supply mode, which helps user operations on the analysis control program 21.

The combination of the code image embedding process and the searching and operation-assisting process additionally produces the following effect: For example, as in the fourth pixel 220, when a piece of information is encoded as the RGB value of one or a plurality of pixels, if the operation-assisting program 22 attempts to directly detect the code image, it is necessary to test the matching of the search target pixel with every possible RGB value of the code image. Such a method is impractical since it incurs a significant amount of processing load as well as increases the probability of incorrectly detecting unrelated pixels as the code image if the code image consists of a small number of pixels. By comparison, in the present embodiment, since the position of the code image is defined with reference to the fixed identification header 210 which is independent of the encoded information, the operation-assisting program 22 only needs to detect this identification header 210. That is to say, the code image can be detected with a high level of accuracy by a search for a single image. Even in the case of using a QR Code as the code image, detecting a sequence of pixels in one row, as with the identification header 210, requires a smaller amount of computation than searching for an image which completely matches with the QR Code which includes a plurality of rows. Consequently, the processing load on the computer in the image search can be reduced by the present embodiment.

For simplification, the previous description has dealt with the configuration in which the analysis control program 21 encodes only the liquid supply mode as the RGB value of the fourth pixel 220, and the operation-assisting program 22 decodes this information and displays a specified setting window. As one application example, the system may be configured so that the analysis control program 21 encodes both the liquid supply mode and the current flow rate of the pump as a QR Code, while the operation-assisting program 22 decodes it and displays the gradient-time-program setting window 600 (FIG. 6) with the value of the flow rate inputted as the "initial concentration".

Second Embodiment

The analysis control device 1 according to the second embodiment of the present invention is described with reference to FIGS. 7-11. The analysis control device 1 according to the present embodiment has the same functional-block configuration as the first embodiment. The difference exists in the form of the identification header displayed by the display controller 35 as well as in the searching method used by the header detector 41.

Figure 7:
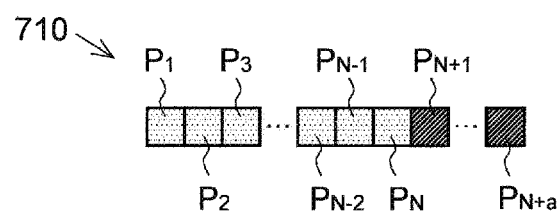
FIG. 7 is one example of the identification header which an analysis control device according to the second embodiment of the present invention embeds in the screen.

FIG. 7 shows one example of the identification header which is embedded in the screen of the monitor 14 by the display controller 35 in the present embodiment. In the identification header 710, all of the N pixels from the first pixel $P_1$ to the Nth pixel $P_N$ (first pixel group) have the same RGB value, while a pixels from the N+1st pixel $P_{N+1}$ to the N+a th pixel $P_{N+a}$ (second pixel group) have an RGB value different from that of the preceding N pixels. The value of N is equal to or greater than three, while the value of a is any number equal to or greater than one. Although the identification header 710 in FIG. 7 is shown as a sequence of pixels in one row, it may be an image that includes a plurality of rows as long as its first row includes an array as shown in the figure. As with the pixels of the identification header 210 in the first embodiment, the specific RGB values of the individual pixels are set so that the pixels have barely noticeable color differences from the neighboring pixels at the embedded position. The flow of the code image embedding process in the present embodiment is basically the same as in the first embodiment (see FIG. 4).

[Flow of Searching and Operation-Assisting Process]

Hereinafter, the flow of the searching and operation-assisting process by the operation-assisting program 22 in the present embodiment is described with reference to FIGS. 8 and 9 which are flowcharts. The timing to initiate the searching and operation-assisting process is the same as in the searching and operation-assisting process in the first embodiment.

Initially, the header detector 41 conducts the search of the pixels in a row (Step S301). Specifically, it refers to the RGB value of pixel (N, 1) in the first row and the Nth column in the captured image of the screen of the monitor 14. The captured image is X pixels wide and Y pixels high, while the code image is W pixels wide and H pixels high.

The header detector 41 searches the row rightward, referring to the RGB value of each pixel (Step S302) to determine whether or not the RGB value has changed from the preceding pixel (Step S304). This determination is achieved by comparing each RGB value with the data of the preceding pixel by executing a function which compares data in the memory area (this function is hereinafter called the "memory comparison function") every time the pixel is moved forward by one column. If the same RGB value has been successively found ("No" in Step S304) the process is returned to Step S302 to continue the search. As a result of Step S302, if the searching point has gone beyond the pixel which is W+a pixels before the right end of the captured image ("Yes" in Step S303), the determination on the change in the RGB value is bypassed and the searching point is moved to the Nth column in the next row (Step S308) before returning to Step S302 to further continue the search. In Step S308, if the searching point has gone below the row which is H−1 rows above the bottom row of the captured image ("Yes" in Step S309), it means that the screen area in which the code image can be detected has been completely searched. Accordingly, the searching and operation-assisting process is discontinued.

It should be noted that the determination in Step S304 is merely concerned with whether or not the RGB value of the search target pixel has changed from the preceding pixel; whether or not the RGB value matches with the N+1st pixel $P_{N+1}$ of the identification header 710 is not included in the determination conditions. If a change in the RGB value from the preceding pixel has been detected ("Yes" in Step S304), the header detector 41 subsequently determines whether or not the search target pixel is the N+1st pixel $P_{N+1}$ of the identification header 710 (Step S305). Specifically, on the assumption that the current search target pixel (x, y) is the N+1st pixel $P_{N+1}$ of the identification header 710, the header detector 41 determines whether or not the sequence of N+a pixels from (x−N, y) to (x+a−1, y) matches with the identification header 710. This determination is achieved by executing the memory comparison function for the sequence of N+a pixels to determine whether or not this sequence matches with the identification header 710. In the case where the identification header 710 is an image which includes a plurality of rows, the matching determination is performed for all rows of the identification header 710 by repeating the process of moving to the next row and similarly executing the memory comparison function after the matching of the first row is confirmed. It should be noted that the processing load incurred by the memory comparison function for a plurality of successive pixels barely differs from that incurred by the memory comparison function used for the pixel-by-pixel comparison in Step S304.

To explain the previously described process more conceptually, the header detector 41 assumes that a pixel at which the RGB value has changed from the preceding pixel is the N+1st pixel $P_{N+1}$ of the identification header 710, and conducts the search to verify this assumption.

That is to say, the reason why the search is initiated from the pixel in the Nth column in Steps S301 and S308 is because no pixel at which a change in the RGB value occurs from one of the pixels in the first through N−1st columns can be the candidate of the N+1st pixel $P_{N+1}$. If the identification header 710 starts from the leftmost end of the captured image, the N+1st pixel $P_{N+1}$ will be detected as the pixel in the N+1st column having a different RGB value from the pixel in the Nth column. Therefore, the pixels at the N−1st and preceding columns do not need to be considered in the comparison process. Accordingly, the search is initiated from the Nth column which is the leftmost possible column where the Nth pixel $P_N$ can be located.

If the sequence of N+a pixels from (x−N, y) to (x+a−1, y) has matched with the identification header 710 ("Yes" in Step S305), the determination result means that the identification header 710 has been detected. Accordingly, the searching and operation-assisting process moves to Step S401 in FIG. 9.

Initially, the code-image detector 42 detects the code image (Step S401). Specifically, an image having a width of W pixels and a height of H pixels located at a predetermined relative position to the identification header 710 (e.g. an image with the upper left pixel located immediately after the N+a th pixel $P_{N+a}$) is recognized as the code image.

Next, the decoder 43 decodes the code image and identifies the analysis parameter (Step S402). Specifically, it refers to the code correspondence table stored in the database 45 and identifies the analysis parameter associated with the code image detected by the code-image detector 42. Alternatively, it may use a specified decoding algorithm to identify the analysis parameter. One specific example of the present step is Step S206 described in the first embodiment.

Next, the operation assistance executer 44 performs a process corresponding to the analysis parameter (Step S403). Specifically, it refers to an operation-assisting process correspondence table (stored in the database 45, although not shown) in which specified items of information are associated with specified processes, and performs the process associated with the analysis parameter specified by the decoder 43. One specific example of the present step is Step S207 described in the first embodiment.

If the identification header has been detected in Step S305, the searching and operation-assisting process is completed. As in the first embodiment, the system may be configured so as to return to Step S302 to further continue the search after Step S403.

Figure 8:
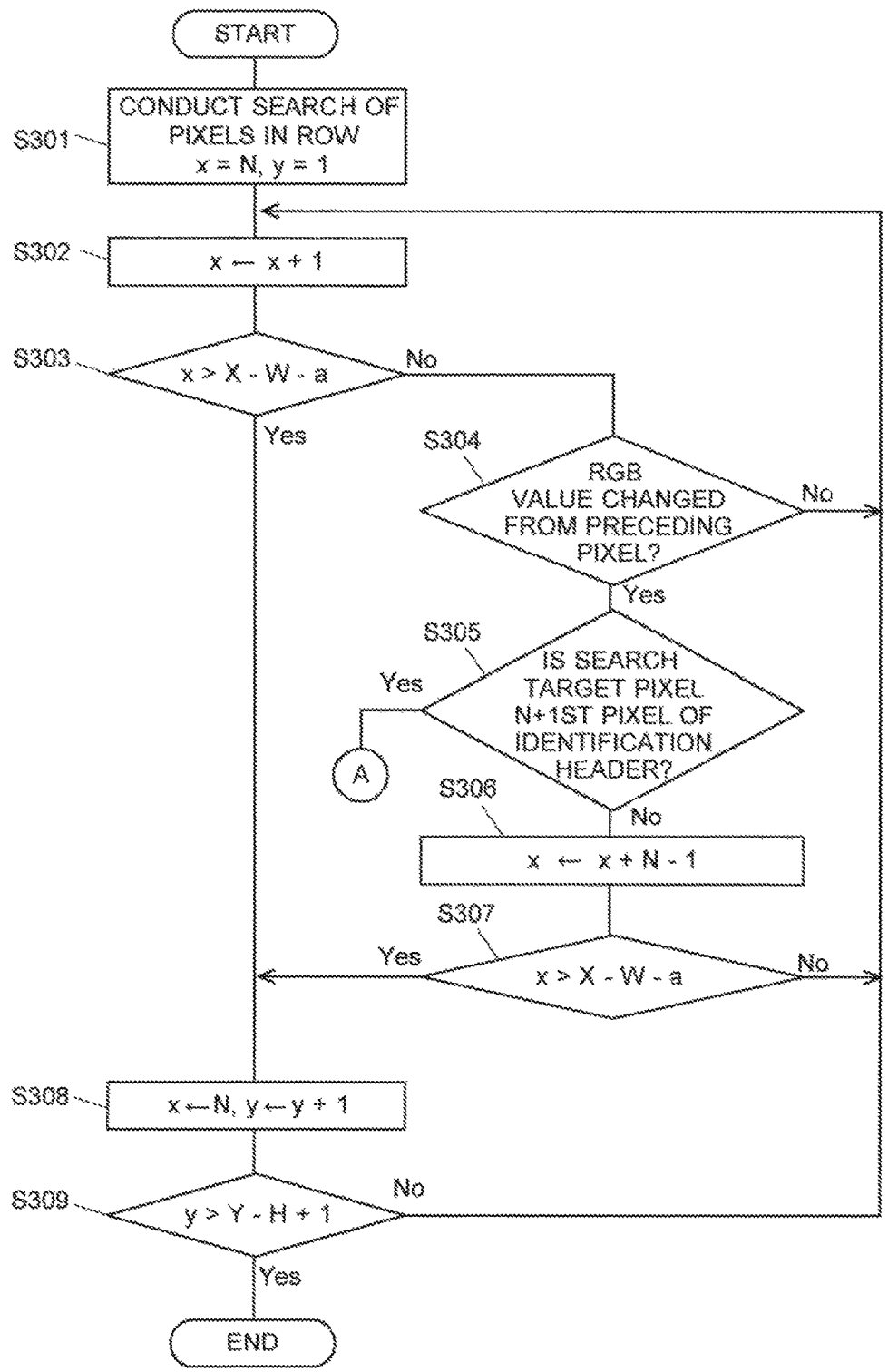
FIG. 8 is a flowchart showing the flow of the searching and operation-assisting process performed by the analysis control device according to the same embodiment.

Once more with reference to FIG. 8, if the sequence of N+a pixels from (x−N, y) to (x+a−1, y) has not matched with the identification header 710 ("No" in Step S305), the header detector 41 moves the searching point forward by N−1 columns (Step S306). Then, if the searching point has not yet gone beyond the pixel which is W+a pixels before the right end of the captured image "Yes" in Step S307), the process is returned to Step S302 to continue the search. As a result of Step S306, if the searching point has gone beyond the pixel which is W+a pixels before the right end of the captured image ("Yes" in Step S307), the process goes to Step S308 and the search is resumed from the Nth column in the next row.

The reason why the searching point is moved forward by N−1 columns in Step S306 is because the N−1 pixels from (x+1, y) to (x+N−1, y) which immediately follow cannot be the N+1st pixel $P_{N+1}$ of the identification header 710. A specific example shown in FIG. 10 is hereinafter described. In the figure, N=5 and a=1. The header detector 41 is searching a row in the direction indicated by the white arrow in the figure. In this search, after the change in the RGB value from the preceding pixel 1000 is detected at the search target pixel 1001 in Step S304, it is determined in Step S305 that the pixel 1001 is not the N+1st pixel $P_{N+1}$ of the identification header 710. In this case, the situation in which the N+1st pixel $P_{N+1}$ is at the closest possible position to the search target pixel 1001 is the case where the search target pixel 1001 is the first pixel $P_1$ of the identification header 710, as shown in FIG. 10. Accordingly, for the same reason why the search in Steps S301 and S308 is initiated from the pixel in the Nth column, the search is resumed from the pixel 1002 which is located N−1 columns ahead and which is the leftmost possible pixel where the Nth pixel $P_N$ can be located in the currently searched row. In FIG. 10, the pixel 1020 which immediately succeeds the identification header 710 is shown as one example of the code image. However, as noted earlier, code images are not limited to the single-pixel form.

According to the processes described to this point, upon detecting two successive pixels having different RGB values in a row, the header detector 41 assumes that the succeeding one of the two pixels is the N+1st pixel $P_{N+1}$ of the identification header 710, and verifies this assumption. If the verification result is negative, the searching point is moved forward by N columns before the search is resumed. In other words, if the pixel selected as the candidate of the N+1st pixel $P_{N+1}$ has been found to be not the N+1st pixel $P_{N+1}$, N−1 pixels can be bypassed in the search. Consequently, the processing load is further reduced. The more non-uniform the RGB values of the pixels in the screen are, the higher the chance of bypassing is. Using a larger value of N increases the number of pixels to be bypassed. Both situations contribute to an improvement in the processing efficiency.

The rate of reduction of the processing load by the present embodiment is hereinafter specifically described. On the assumption that the identification header 710 cannot be detected within the captured image and the entire screen needs to be completely searched, the number of executions of the memory comparison function, which is the primary cause of the increase in the processing load in the search, is compared between the case where the present embodiment is not used and the case where it is used. The "case where the present embodiment is not used" is the case where the technique as described in the first embodiment is adopted in which the pixels on the screen are individually examined to locate an image which completely matches with the identification header.

Let X and Y respectively denote the pixel width and pixel height of the captured image, while Wq and Hq respectively denote the pixel width and pixel height of the rectangular area which includes both the identification header 710 and the code image. Additionally, let P denote the percentage (%) of the pixels having a different RGB value from the preceding one in the row direction on the captured image. In the case where the present embodiment is not used, the processing load Q1 is expressed by the following equation (3):

$$Q1=(X-Wq)*(Y-Hq) \tag{3}$$

The reason why Wq and Hq are subtracted is to exclude the case where the identification header 710 or the code image is not entirely included in the screen.

In the case where the present embodiment is used, the processing load Q2 is expressed by the following equation (4):

$$Q2=\{(100-P)+P*2/N\}*(X-Wq)*(Y-Hq)/100 \tag{4}$$

As can be understood from equations (3) and (4) when P=0, i.e. when all pixels in the captured image have the same RGB value, the present embodiment produces no reduction in the processing load. However, such a situation is almost impossible in practical applications. Accordingly, P is likely to have a value within a range from 20 to 90.

FIG. 11 shows the processing load required for the search of the identification header 710 in the case where the present embodiment is used. The shown values are relative values, with unity (1) indicating the processing load in the case where the present embodiment is not used. As shown, the larger the value of P is, or the larger the value of N is, the lower the processing load becomes.

Third Embodiment

The analysis control device 1 according to the third embodiment of the present invention is described with reference to FIGS. 12-16. The analysis control device 1 according to the present embodiment has the same functional-block configuration as the first embodiment. As for the form of the identification header displayed by the display controller as well as the searching method used by the header detector 41, additional modifications are made to those of the second embodiment.

FIG. 12 shows one example of the identification header which is embedded in the screen of the monitor 14 by the display controller 35 in the present embodiment. In the identification header 1210, all of the N pixels from the first pixel $P_1$ to the Nth pixel $P_N$ (first pixel group) have the same RGB value, while M pixels from the N+1st pixel $P_{N+1}$ to the N+Mth pixel $P_{N+M}$ (second pixel group) have an RGB value (Mr, Mg, Mb) different from that of the preceding N pixels. The value of N is equal to or greater than three, while the value of M is greater than N. As in the second embodiment, the identification header 1210 may be an image which includes a plurality of rows. The flow of the code image embedding process in the present embodiment is basically the same as the first embodiment (see FIG. 4). As with the pixels of the identification header 210 in the first embodiment, the specific RGB values of the individual pixels are set so that the pixels have barely noticeable color differences from the neighboring pixels at the embedded position.

Additionally, the RGB value (Mr, Mg, Mb) of those M pixels should preferably be a value that is rarely used on the screen of the monitor 14. For example, a color which satisfies Mr=Mg=Mb is popularly used on Windows®, whereas a color which satisfies Mr≠Mg, Mg≠Mb and Mb≠Mr is less likely used. Accordingly, an RGB value which satisfies the latter three formulae should be assigned.

[Flow of Searching and Operation-Assisting Process]

Hereinafter, the flow of the searching and operation-assisting process by the operation-assisting program 22 in the present embodiment is described with reference to FIGS. 13 and 14 which are flowcharts. The timing to initiate the searching and operation-assisting process is the same as in the searching and operation-assisting process in the first embodiment.

Figure 13:
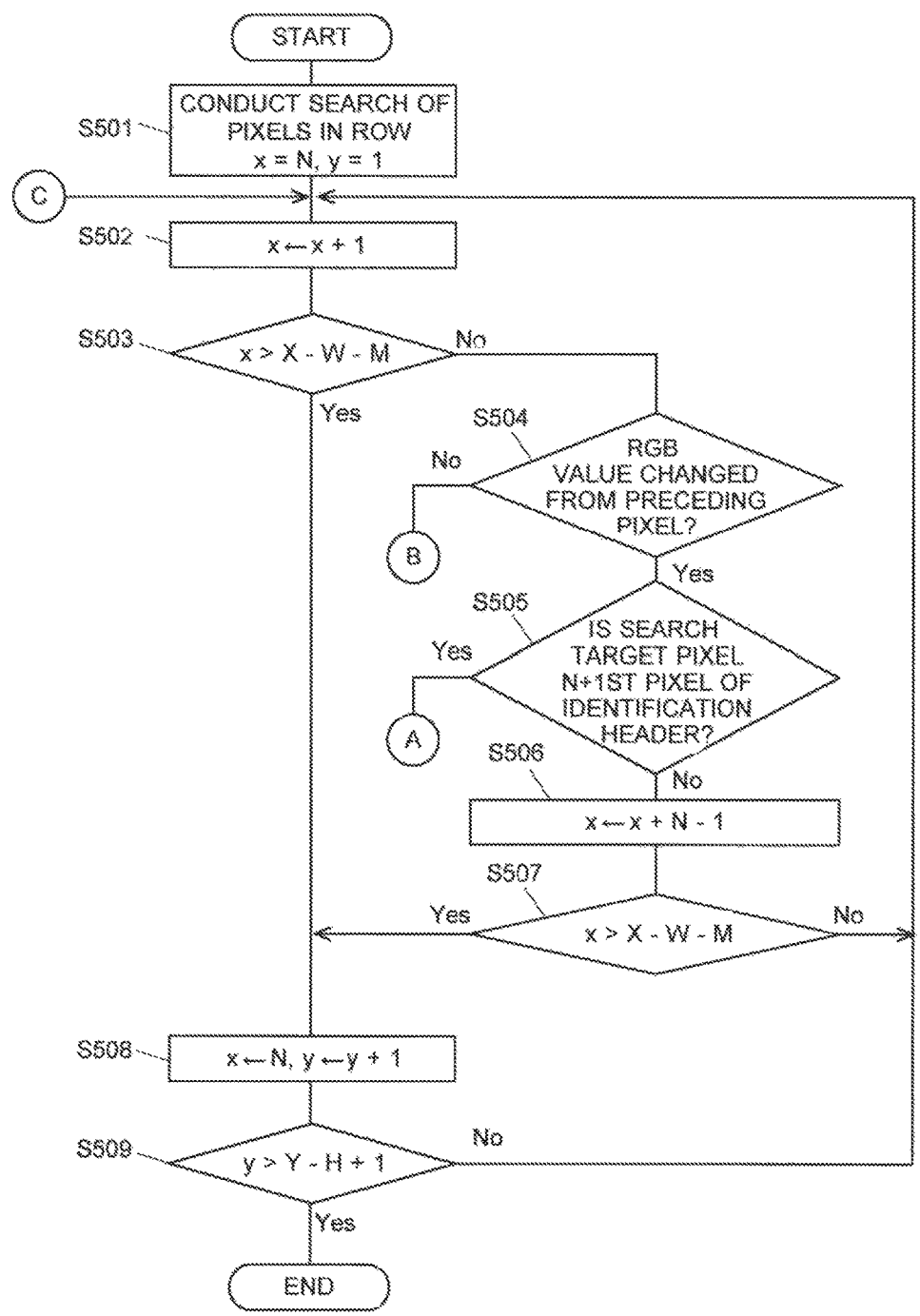
FIG. 13 is a flowchart showing the flow of the searching and operation-assisting process performed by the analysis control device according to the same embodiment.

The processes in Steps S501-S503 and S505-S509 shown in FIG. 13 are basically the same as Steps S301-S303 and S305-S309 described in the second embodiment with reference to FIG. 8. Constant a is replaced by M in Steps S503 and S507. This reflects the difference in the number of pixels subsequent to the N+1st pixel $P_{N+1}$ in the identification headers 710 and 1210. The replacement of a by M should also be applied in the other Steps.

The content of the determination process in Step S504 is also similar to Step S304. However, in the present embodiment, if it is determined that the RGB value has not changed from the preceding pixel ("No" in Step S504), i.e. if two successive pixels having the same color have been found, the header detector 41 does not immediately begin the search for the next pixel but proceeds to Step S601 shown in FIG. 14.

If two successive pixels having the same color have been found, the header detector 41 moves the searching point forward by M columns (Step S601). Then, it determines whether or not the RGB value of the current search target pixel matches with that of the M pixels from the N+1st pixel $P_{N+1}$ to the N+Mth pixel $P_{N+M}$ (Step S602). Specifically, provided that the search target pixel in Step S504 is at (x, y), whether or not the RGB value at (x+M, y) is (Mr, Mg, Mb) is determined. If the two values are the same ("Yes" in Step S602) the searching point is moved backward by M columns (Step S604) i.e. to pixel (x, y), and subsequently, the process is returned to Step S502 to continue the search.

If the RGB value of the pixel (x+M, y) which is reached after the searching point is moved forward by M columns in Step S601 is equal to (Mr, Mg, Mb) which is rarely used outside the identification header 1210, the pixel (x+M, y) is most likely to be one of the aforementioned M pixels of the identification header 1210. In this situation, the N+1st pixel $P_{N+1}$ of the identification header 1210 is likely to be located at a close position succeeding the pixel (x, y). Therefore, in Step S604, the searching point is returned to pixel (x, y). In other words, in the present embodiment, upon detecting two successive pixels having the same RGB value, the header detector 41 assumes that they are the first and second pixels P1 and P2 of the identification header 1210 or other pixels near P1 and P2, and conducts the search to verify this assumption.

On the other hand, if the RGB value of the search target pixel is not (Mr, Mg, Mb), i.e. if "No" in Step S602, the header detector 41 moves the searching point backward by N columns (Step S603); i.e. it selects (x+M−N, y) as the search target pixel, and returns to Step S502 to continue the search.

The reason why M−N−1 pixels which succeed (x, y) are not selected as the search target pixel when the determination result in Step S602 is negative is because those pixels cannot be candidates of the pixels included in the identification header 1210. A specific example shown in FIG. 15 is hereinafter described. In the figure, N=3 and M=6. The header detector 41 is searching a row in the direction indicated by the white arrow in the figure. In this search, after the search target pixel 1501 is found to have the same RGB value as the preceding pixel 1500 in Step S504, it is determined in Step S602 that the RGB value of pixel 1502 which is ahead of the search target pixel 1501 by six columns is not (Mr, Mg, Mb). In this case, the situation in which the first one of the M pixels of the identification header 1210 (i.e. the N+1st pixel $P_{N+1}$) is at the closest possible position to the search target pixel 1502 is the case where the search target pixel 1502 is the Nth pixel $P_N$ of the identification header 1210, as shown in FIG. 15. If this is the case, the pixel which immediately precedes the identification header 1210 should be located at pixel 1503 which is three columns before the search target pixel 1502. Accordingly, the searching point is moved backward by N columns to pixel 1503. After that, if the pixel 1504 which immediately follows (i.e. the first pixel $P_1$) actually has an RGB value different from pixel 1503 ("Yes" in Step S504), the searching point is moved to the Nth pixel $P_N$ of the identification header 1210 through Steps S505 and S506, and subsequently, the N+1st pixel $P_{N+1}$ which immediately follows is detected by Steps S502 through S505. In FIG. 15, the pixel 1520 which immediately succeeds the identification header 1210 is shown as one example of the code image. However, as already noted, code images are not limited the single-pixel form.

According to the processes described to this point, the header detector 41 performs the following operation in addition to the configurations described in the second embodiment: If two successive pixels having the same RGB value have been detected in a row, it is assumed that these two pixel are the first and second pixels P1 and P2 of the identification header 1210 or other pixels near P1 and P2. Subsequently, the searching point is moved from the succeeding one of the two pixels to the pixel which is M columns ahead. Then, it is determined whether or not the RGB value of this pixel is the same as the RGB value of the M pixels from the N+1st pixel $P_{N+1}$ to the N+Mth pixel $P_{N+M}$ of the identification header 1210. If the two values are the same, the searching point is moved backward from the current position by M−1 columns, i.e. to the pixel which immediately succeeds the original position, and the search is continued. If the two values are not the same, the searching point is moved backward from the current position by N−1 columns, i.e. to the pixel which is M−N+1 columns ahead of the original position, and the search is continued. This means that, if it is determined that the identification header 1210 is not located at a close position succeeding the two aforementioned pixels, M−N pixels can be bypassed in the search. Consequently, the processing load is further reduced. Providing a larger difference between M and N increases the number of pixels to be bypassed, which contributes to an improvement in the processing efficiency.

The rate of reduction of the processing load by the present embodiment is specifically described. The method of comparison is the same as in the previous embodiment. In the case where the present embodiment is not used, the processing load Q1 is expressed by equation (3). In the case where the present embodiment is used, the processing load Q3 is expressed by the following equation (5):

$$Q3=\{(100-P)*2/(M-N)+P*2/N\}*(X-Wq)*(Y-Hq)/100 \qquad (5)$$

FIG. 16 shows the processing load required for the search of the identification header 1210 in the case where the present embodiment is used. The shown values are relative values, with unity (1) indicating the processing load in the case where the present embodiment is not used. For convenience, the condition of M=2N is applied, in which case the rate of reduction of the processing load is independent of the value of P. According to equations (4) and (5), Q3 is equal to Q2 when M=N+2. Therefore, the rate of reduction will be higher than in the second embodiment if N+2<M.

Specific examples of the processing efficiency for different forms of the identification header 1210 are as follows: If an image which is 20 pixels wide and 20 pixels high is used as the identification header 1210, the processing load is reduced to approximately 30% of the case where the present embodiment is not used. If a sequence of 60 pixels continuously arranged in a row is used as the identification header 1210, the processing load is reduced to approximately 10% of the case where the present embodiment is not used. The processing efficiency improves with an increase in the width N+M of the identification header 1210, while an increase in its height does not contribute to the improvement in the processing efficiency. This is due to the fact that the search by the header detector 41 is the scan in the row direction.

[Variations]

Any of the previous embodiments is premised on that the operation-assisting program 22 is used along with the analysis control program 21, and the RGB value of each pixel in the identification header is previously known to the operation-assisting program 22. However, the following configuration will also be useful if the operation-assisting program 22 is intended for use with a variety of software products.

For example, if the RGB values assigned to the code image and the identification header are not previously known, the header detector 41 may detect, as the identification header, a group of pixels having specific color differences within a specified size of area in which almost all pixels have the same RGB value (which is hereinafter called the "background color"). Specifically, in the case of FIGS. 3A and 3B, when three successive pixels which respectively have the RGB values of (R+1, G+1, B+1), (R−1, G−1, B−1) and (R+2, G+2, B+2) are detected within a designated area with a background color of (R, G, B), this group of pixels is recognized as the identification header 210. The decoding of the information held by the fourth pixel 220 can also be performed based the differences from the background color. In the case where the code image is a QR Code, the color difference between the pixels constituting the QR Code and the background color can be previously specified. By adopting such configurations, it becomes possible to assist user operations for various UI (user interface) designs if there is previous knowledge about the color difference of each pixel from the background color as well as the correspondence relationship between the color difference and the coded information.

It should be noted that the previously described embodiments and variations are mere examples of the present invention, and any change, modification, addition or combination appropriately made within the spirit of the present invention will naturally fall within the scope of claims of the present application.

For example, as opposed to the previously described embodiments in which the identification header is placed immediately before the upper left end of the code image, the identification header may be placed immediately before the lower left end of the code image or immediately after the upper right or lower right end of the code image. A plurality of kinds of identification headers may be simultaneously displayed on the screen of the monitor 14, with the header detector 41 configured to detect each of them.

REFERENCE SIGNS LIST

1 . . . Analysis Control Device
21 . . . Analysis Control Program
22 . . . Operation-Assisting Program
34 . . . Encoder
35 . . . Display Controller
41 . . . Header Detector
42 . . . Code-image Detector
43 . . . Decoder
44 . . . Operation Assistance Executer
210, 710, 1210 . . . Identification Header
220 . . . Fourth Pixel
1020, 1520 . . . Code Image

The invention claimed is:

1. An information display processing device for displaying a predetermined process result on a screen of a display unit, comprising:
   a) an encoding section for creating a code image by encoding a piece of information held in the device; and
   b) a display control section for displaying, on the screen, the code image created by the encoding section and a single identification header in a predetermined positional relationship to the code image,
   wherein the single identification header holds only information which enables locating the code image;
   wherein the code image and the identification header are composed of a plurality of pixels having color differences which are difficult to be visually recognized by users; and
   wherein the display control section displays the code image and the identification header in a uniformly-colored area within a designated region occupied by a color close to the plurality of pixels.

2. The information display processing device according to claim 1, wherein:
   the identification header includes a first pixel group composed of N uniformly-colored pixels sequentially arranged in a row direction and a second pixel group neighboring the first pixel group in the same row, with the second pixel group composed of one or a plurality of pixels having a different color from the first pixel group, where N is a natural number equal to or greater than three.

3. The information display processing device according to claim 2, wherein:
   the second pixel group may be composed of M uniformly-colored pixels sequentially arranged in the row direction, where M is a natural number greater than N.

4. An operation-assisting device for assisting user operations related to a target software, comprising:
   a) an identification-header detection section for detecting a single identification header displayed on a screen of a display unit, the single identification header being in a predetermined positional relationship to a code image, and holding only information which enables locating the code image;
   b) a code-image detection section for detecting, based on the predetermined positional relationship with the identification header detected by the identification-header detection section, the code image in which a specified item of information related to the target software is held in a coded form;
   c) a decoding section for decoding the code image detected by the code-image detection section, to obtain the specified item of information; and
   d) an execution section for performing a specified process associated with the specified item of information obtained by the decoding section wherein the code image and the identification header are composed of a plurality of pixels having color differences which are difficult to be visually recognized by users; and wherein the display unit displays the code image and the identification header in a uniformly-colored area within a designated region occupied by a color close to the plurality of pixels.

5. The operation-assisting device according to claim 4, wherein:

the identification-header detection section is configured so that, for a natural number N equal to or greater than three, the identification-header detection section searches the screen in the row direction, examining a value of each pixel, and if a pixel whose color differs from a preceding pixel is detected, the identification-header detection section determines whether or not the detected pixel is a pixel in an N+1st column of the identification header, and if a determination result is negative, the identification-header detection section resumes the search from a pixel which is N columns far ahead of the detected pixel.

6. The operation-assisting device according to claim 5, wherein:
the identification-header detection section is further configured so that, for a natural number M greater than N, if a pixel having the same color as a preceding pixel is detected, the identification-header detection section determines whether or not a color of a pixel located M columns far ahead of the detected pixel is a same as a color of pixels in N+1 st through N+Mth columns of the identification header, and then resumes the search from a pixel located immediately after the detected pixel if it is determined that the two colors are the same, or from a pixel located M−N+1 columns far ahead of the detected pixel if it is determined that the two colors are different from each other.

7. A non-transitory computer readable medium recording a control program for making a computer function as the sections of the information display processing device according to claim 1.

8. A non-transitory computer readable medium recording a control program for making a computer function as the sections of the operation-assisting device according to claim 4.

9. The information display processing device according to claim 1, wherein:
the identification header includes a first pixel group composed of N uniformly-colored pixels sequentially arranged in a row direction and a second pixel group neighboring the first pixel group in the same row, with the second pixel group composed of one or a plurality of pixels having a different color from the first pixel group, where N is a natural number equal to or greater than three.

10. The information display processing device according to claim 9, wherein:
the second pixel group may be composed of M uniformly-colored pixels sequentially arranged in the row direction, where M is a natural number greater than N.

11. A non-transitory computer readable medium recording a control program for making a computer function as the sections of the information display processing device according to claim 1.

12. A non-transitory computer readable medium recording a control program for making a computer function as the sections of the information display processing device according to claim 2.

13. A non-transitory computer readable medium recording a control program for making a computer function as the sections of the information display processing device according to claim 3.

14. A non-transitory computer readable medium recording a control program for making a computer function as the sections of the information display processing device according to claim 9.

15. A non-transitory computer readable medium recording a control program for making a computer function as the sections of the information display processing device according to claim 10.

16. A non-transitory computer readable medium recording a control program for making a computer function as the sections of the operation-assisting device according to claim 5.

17. A non-transitory computer readable medium recording a control program for making a computer function as the sections of the operation-assisting device according to claim 6.

18. An operation-assisting device for assisting user operations related to a target software, comprising:
(i) an information display processing device for displaying a predetermined process result on a screen of a display unit, the information display processing device including:
a) an encoding section for creating a code image by encoding a piece of information held in the device; and
b) a display control section for displaying, on the screen, the code image created by the encoding section and a single identification header in a predetermined positional relationship to the code image,
wherein the single identification header holds only information which enables locating the code image;
wherein the code image and the identification header are composed of a plurality of pixels having color differences which are difficult to be visually recognized by users; and
wherein the display control section displays the code image and the identification header in a uniformly-colored area within a designated region occupied by a color close to the plurality of pixels;
(ii) an identification-header detection section for detecting a single identification header displayed on a screen of a display unit, the single identification header being in a predetermined positional relationship to a code image, and only holding information which enables locating the code image;
(iii) a code-image detection section for detecting, based on the predetermined positional relationship with the identification header detected by the identification-header detection section, the code image in which a specified item of information related to the target software is held in a coded form;
(iv) a decoding section for decoding the code image detected by the code-image detection section, to obtain the specified item of information; and
(v) an execution section for performing a specified process associated with the specified item of information obtained by the decoding section,
wherein the identification-header detection section is configured so that, for a natural number N equal to or greater than three, the identification-header detection section searches the screen in the row direction, examining a value of each pixel, and if a pixel whose color differs from a preceding pixel is detected, the identification-header detection section determines whether or not the detected pixel is a pixel in an N+1 st column of the identification header, and if a determination result is negative, the identification-header detection section resumes the search from a pixel which is N columns far ahead of the detected pixel.

19. The operation-assisting device according to claim 18, wherein:

the identification-header detection section is further configured so that, for a natural number M greater than N, if a pixel having the same color as a preceding pixel is detected, the identification-header detection section determines whether or not a color of a pixel located M columns far ahead of the detected pixel is a same as a color of pixels in N+1 st through N+Mth columns of the identification header, and then resumes the search from a pixel located immediately after the detected pixel if it is determined that the two colors are the same, or from a pixel located M−N+1 columns far ahead of the detected pixel if it is determined that the two colors are different from each other.

20. A non-transitory computer readable medium recording a control program for making a computer function as the sections of the operation-assisting device according to claim 18.

21. A non-transitory computer readable medium recording a control program for making a computer function as the sections of the operation-assisting device according to claim 18.

22. A non-transitory computer readable medium recording a control program for making a computer function as the sections of the operation-assisting device according to claim 19.

* * * * *